United States Patent
Min

(10) Patent No.: US 11,090,397 B2
(45) Date of Patent: Aug. 17, 2021

(54) INTEGRATED PLATELET COLLECTION AND PATHOGEN INACTIVATION PROCESSING SYSTEMS AND FLUID CIRCUITS

(71) Applicant: Fenwal, Inc., Lake Zurich, IL (US)

(72) Inventor: Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 49 days.

(21) Appl. No.: 16/152,580

(22) Filed: Oct. 5, 2018

(65) Prior Publication Data

US 2019/0105413 A1 Apr. 11, 2019

Related U.S. Application Data

(60) Provisional application No. 62/569,372, filed on Oct. 6, 2017.

(51) Int. Cl.
| | | |
|---|---|---|
| A61L 2/00 | (2006.01) | |
| A61M 1/36 | (2006.01) | |
| A61M 1/38 | (2006.01) | |
| A61L 12/00 | (2006.01) | |
| A61M 1/02 | (2006.01) | |

(52) U.S. Cl.
CPC ........... *A61L 2/0047* (2013.01); *A61L 2/0076* (2013.01); *A61L 12/00* (2013.01); *A61M 1/0209* (2013.01); *A61M 1/3683* (2014.02); *A61M 1/3693* (2013.01); *A61M 1/38* (2013.01); *A61L 2202/22* (2013.01); *A61M 2202/0427* (2013.01); *A61M 2205/12* (2013.01)

(58) Field of Classification Search
CPC .. A61L 2/0047; A61L 2/20076; A61L 2/0076; A61M 1/38; A61M 1/3683; A61M 1/3693
See application file for complete search history.

(56) References Cited

U.S. PATENT DOCUMENTS

| | | | |
|---|---|---|---|
| 5,427,509 | A | 6/1995 | Chapman et al. |
| 6,312,607 | B1 | 11/2001 | Brown et al. |
| 6,582,349 | B1 | 6/2003 | Cantu et al. |
| 7,025,877 | B1 | 4/2006 | de Gheldere et al. |
| 7,445,756 | B2 | 11/2008 | Moore et al. |
| 9,402,866 | B2 | 8/2016 | Radwanski et al. |
| 2006/0221330 | A1 | 10/2006 | Waldo et al. |
| 2009/0211987 | A1 | 8/2009 | Min |

FOREIGN PATENT DOCUMENTS

EP 2620171 A1 7/2013

OTHER PUBLICATIONS

Extended European Search Report by the European Patent Office for European Patent Application No. 18198639.9, dated Jun. 25, 2019 (10 pages).

*Primary Examiner* — Sean E Conley
(74) *Attorney, Agent, or Firm* — Cook Alex Ltd.

(57) ABSTRACT

A fluid processing system including an integrated blood component collection and pathogen inactivation fluid circuit is disclosed.

10 Claims, 7 Drawing Sheets

INTEGRATED PLATELET COLLECTION AND PATHOGEN INACTIVATION PROCESSING SYSTEMS AND FLUID CIRCUITS

CROSS-REFERENCE TO RELATED APPLICATION

This application claims the benefit of and priority to U.S. Provisional Patent Application Ser. No. 62/569,372, filed on Oct. 6, 2017, the disclosure of which is incorporated herein by reference in its entirety.

FIELD OF THE DISCLOSURE

The present disclosure is directed to integrated systems and methods for processing blood components and pathogen inactivation.

BACKGROUND

Kits for use in the pathogen inactivation of a blood component are described in U.S. Pat. Nos. 7,025,877 and 7,445,756, the contents of both of which are incorporated herein by reference. As shown in the these patents, the kits typically include an illumination container, a container housing a compound adsorption device and a container for receiving the treated component from the container housing the compound adsorption device. In addition, a container housing the photoactive agent is also included in the kit.

Currently, parts of the kit must be sterilized by different forms of sterilization. Inasmuch as the container housing the photoactive agent comprises the "wet" side of the kit and the remainder of the pathogen inactivation kit comprises a "dry" side of the kit, a single form of sterilization is not used. The wet side is typically subjected to steam sterilization while the dry side is radiation sterilized as shown in FIGS. 1 and 2. The two "sides" are then brought together and joined in a sterile manner as shown in FIG. 3. The now-integrated kit may then be connected to a source of platelets suspended in plasma, an additive solution or some combination of plasma and the additive solution.

The process of sterilizing and joining the wet and dry "sides" of the pathogen inactivation kit and then further connecting the collected platelet product is cumbersome and time-consuming. Thus, it would be desirable to provide a system and method for providing an integrated fluid circuit that eliminates the need to connect the respective wet and dry sides of the pathogen inactivation kit. It would also be desirable to provide a fluid circuit that integrates the platelet collection portion of the method with the of the pathogen inactivation components such as the illumination container, the compound adsorption device and the final storage container. In addition, it would be desirable to provide a system and method that allows for delivery of the photoactive agent and the additive solution to the integrated fluid circuit. It would also be desirable to provide a method for assembling a combined platelet collection pathogen inactivation kit where all "wet" components can be sterilized by steam sterilization and all "dry" components can be sterilized by radiation sterilization.

SUMMARY

The present disclosure is directed to a fluid processing system comprising a reusable hardware unit comprising a separator and an integrated fluid circuit. The fluid circuit is configured for mounting onto the reusable hardware unit. The circuit comprises one or more fluid processing cassettes, a blood access device, a separation chamber and a blood component illumination/collection container wherein said container is made of a material that is configured to transmit light of a selected wavelength.

The present disclosure is also directed to a method for providing a pathogen-inactivation ready product. The method includes mounting the integrated fluid circuit of the type described above onto a reusable hardware unit including a blood component separator; collecting one or more doses of platelets in said illumination/collection container; attaching a source of photoactivation agent and additive solution to said integrated fluid circuit; and combining said photoactive agent and said additive solution with said one or more platelet doses.

DETAILED DESCRIPTION OF THE EMBODIMENTS

Figure 1:
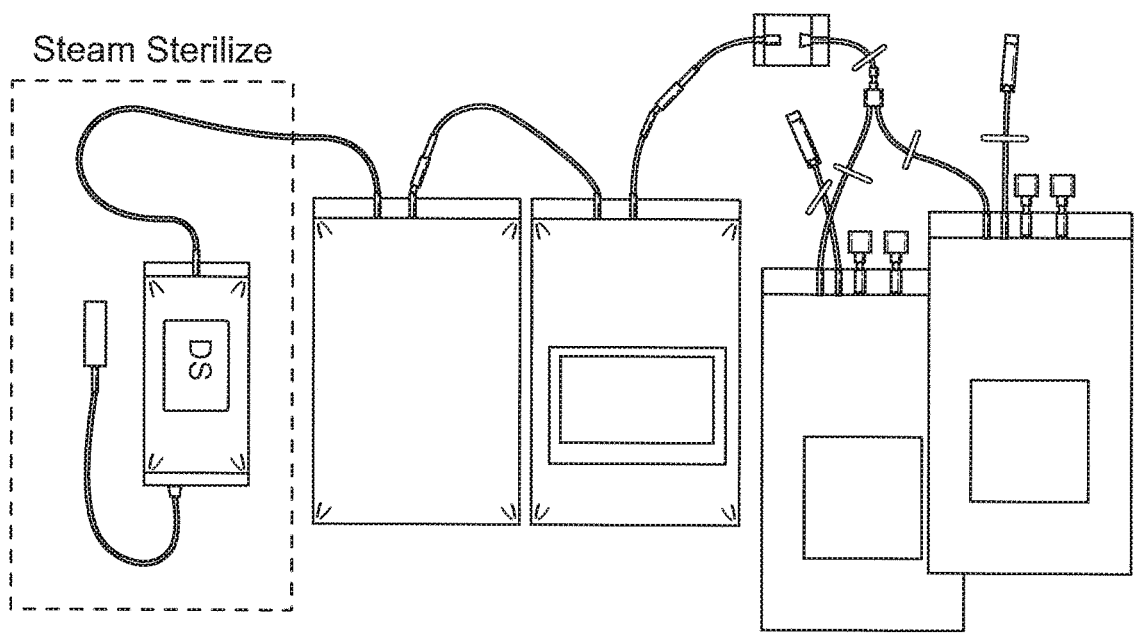
FIG. 1 is a diagram of an assembled pathogen inactivation kit wherein the container of photoactive agent (the "wet" side) has been steam sterilized.
Figure 2:
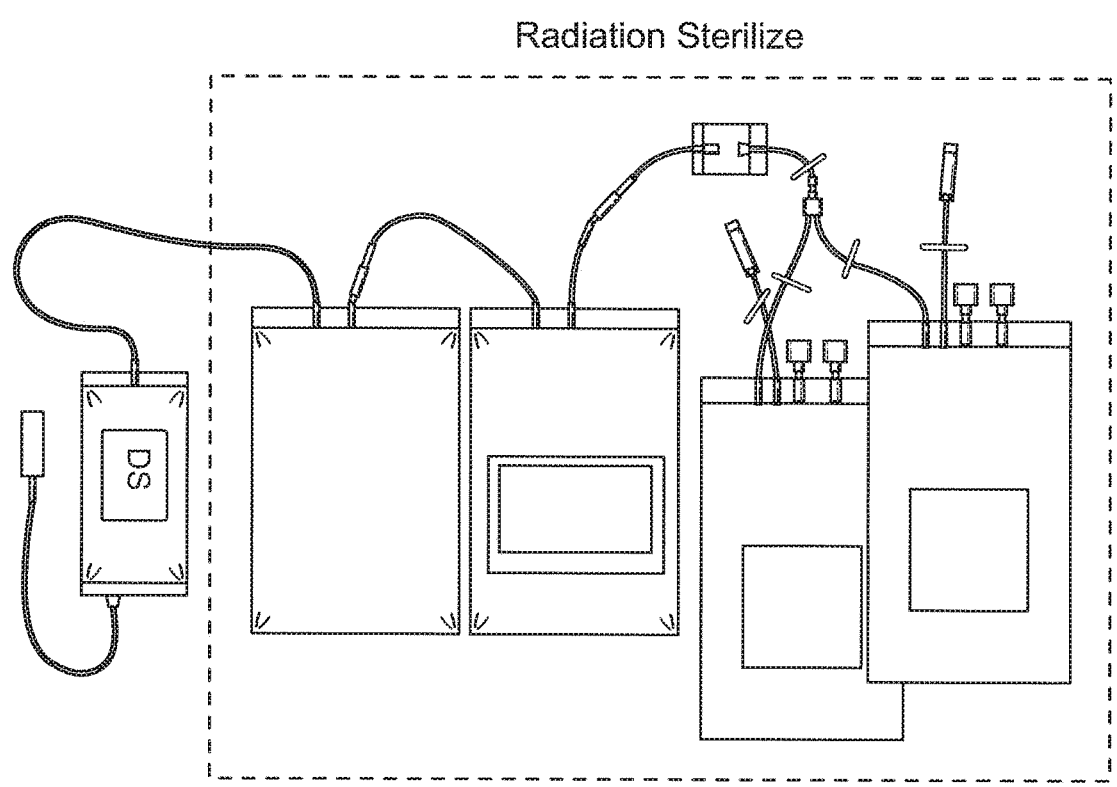
FIG. 2 is a diagram of the kit of FIG. 1 wherein the remainder of the kit (the "dry" side) has been sterilized by radiation sterilization.
Figure 3:
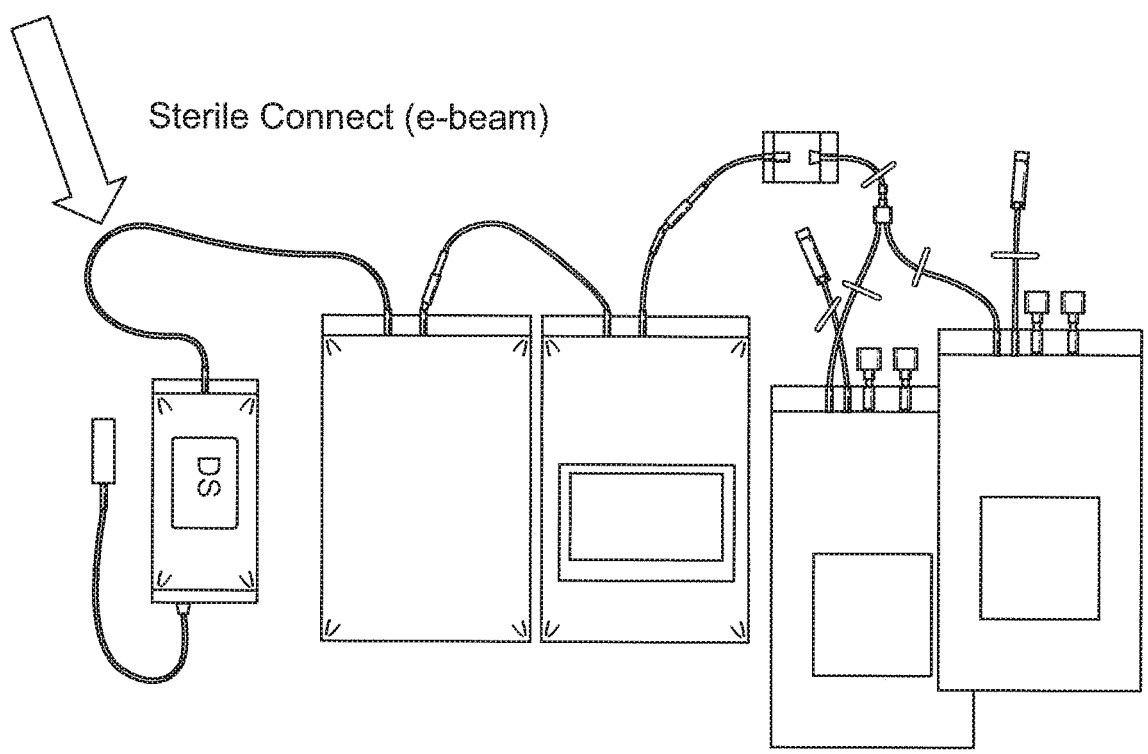
FIG. 3 is diagram of the kit of FIGS. 1 and 2 showing the connection of the "wet" side with the "dry" side of the kit.

As described above and shown in FIGS. 1-3 above, currently, certain pathogen inactivation kits must be sterilized by different forms of sterilization. The different "sides" of the kit are then connected in a sterile fashion using for example e-beam sterile connection (FIG. 3).

Figure 5:
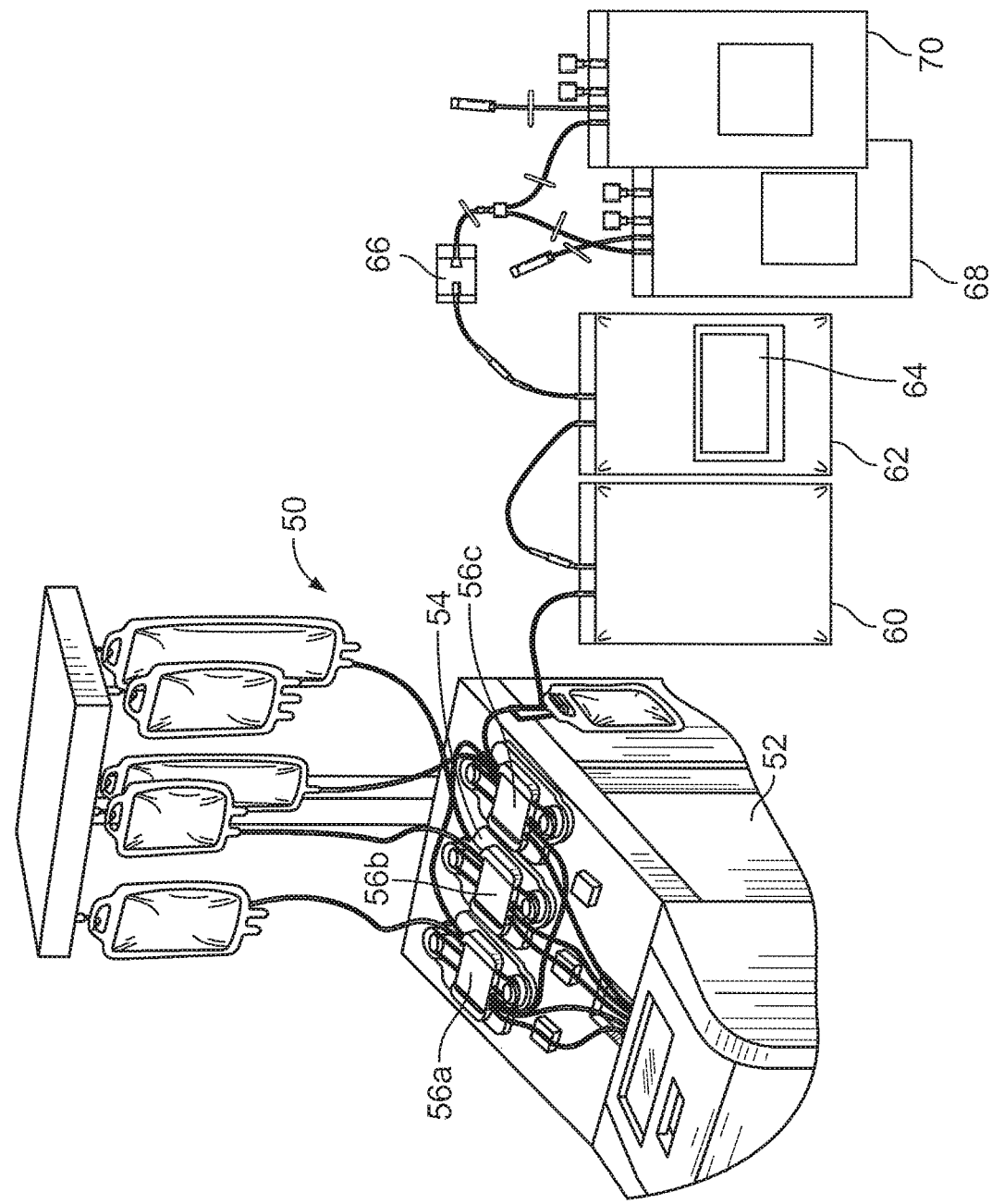
FIG. 5 is a partial view of the reusable hardware unit with the integrated fluid circuit mounted thereon.
Figure 6:
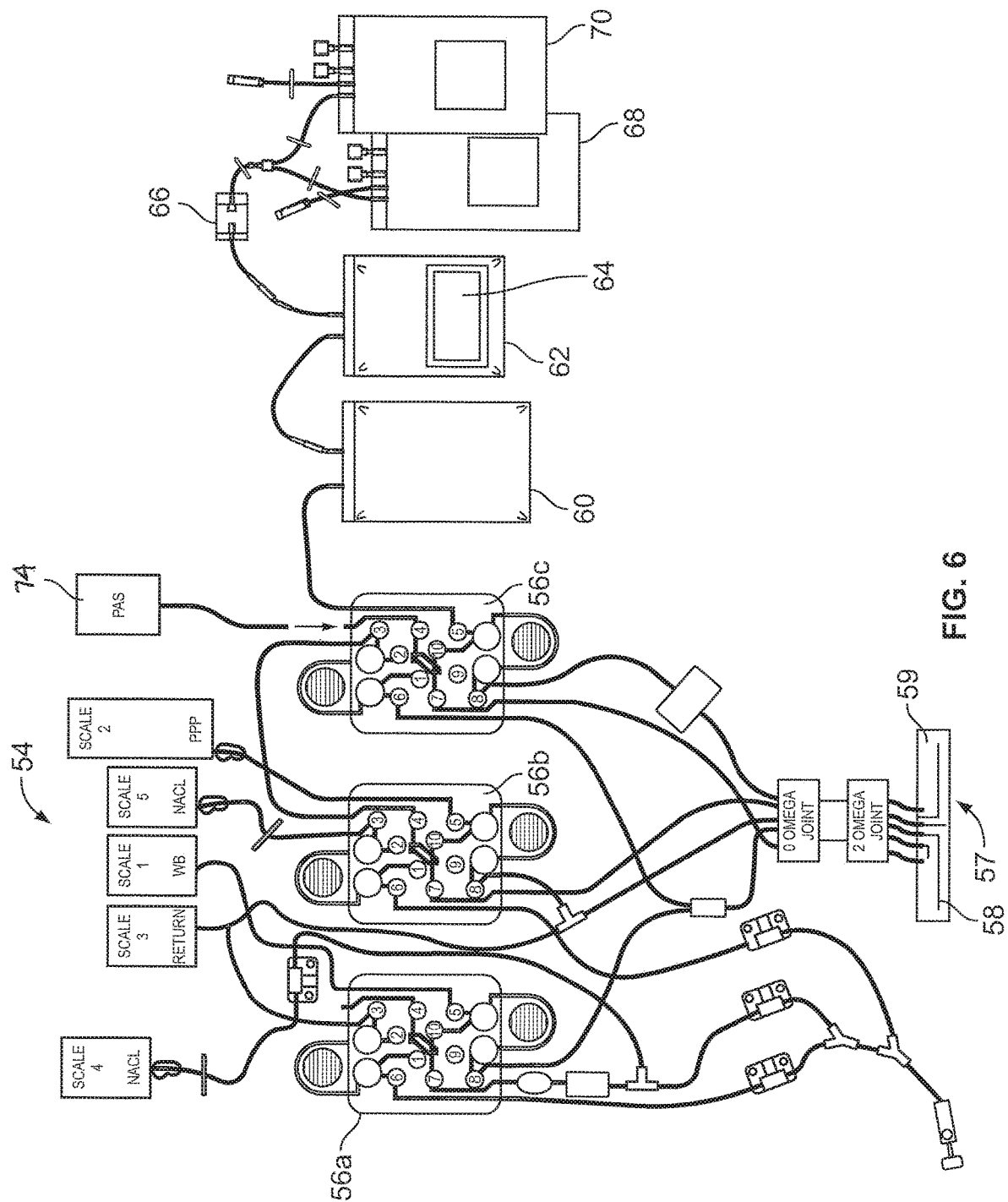
FIG. 6 is a diagram of the integrated fluid circuit in accordance with the present disclosure.

In accordance with the present disclosure, the pathogen inactivation "kit" and/or the components thereof may be integrated with the fluid circuit used to collect the blood component (e.g., platelets). As shown in FIGS. 5 and 6, integrated fluid circuit 54 includes pre-attached illumination/collection container 60. Container 60 should be made of a material that is able to transmit light of a selected wavelength for the particular pathogen inactivation process (e.g., UVA). Container 60 is preferably sized to receive one or more doses of the collected blood component, such as platelets.

Downstream of and in openable flow communication with container 60 is container 62 which houses compound adsorption device 64 (as described in U.S. Pat. Nos. 7,025,877 and 7,445,756). Further downstream of container 62, the integrated fluid circuit 54 may include filter 66 and final component collection containers 68 and 70.

Figure 7:
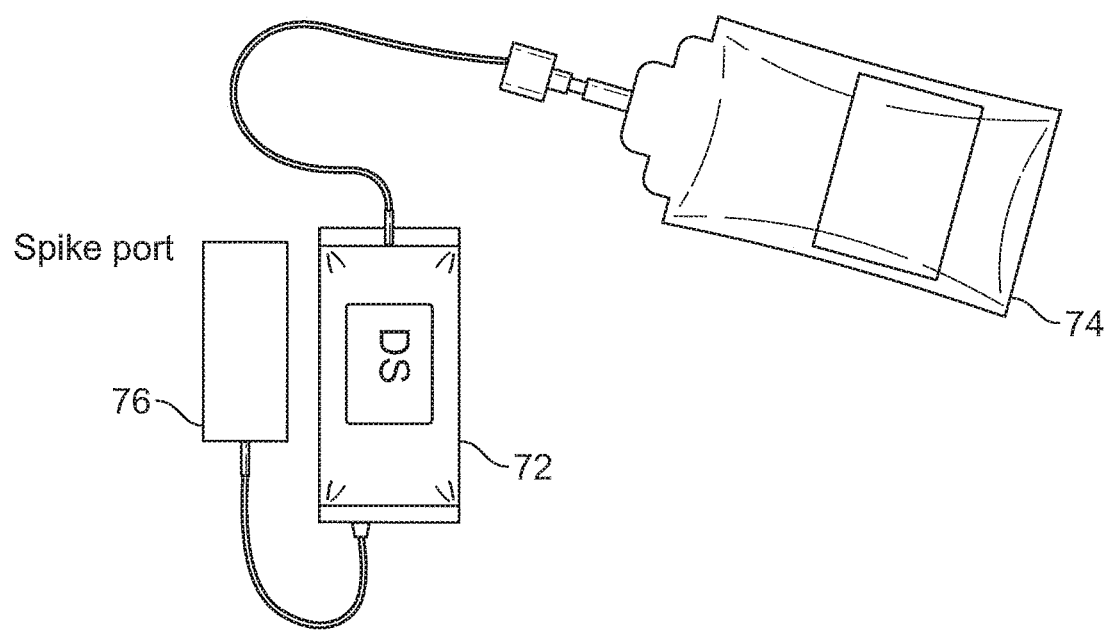
FIG. 7 is a diagram of the container of additive solution with a source of photoactive agent associated therewith and a spike port for accessing the fluid circuit.

As further shown in FIG. 7, the container 72 of photoactive agent (which is preferably wrapped in a light impermeable film) need not initially be part of or associated with the illumination container 60. Thus, sterile connection of container 72 to illumination container 60 (as depicted in the system of FIG. 3) is not required. In accordance with the present disclosure, container 72 may instead be associated with container 74 that holds the additive solution such as a platelet additive solution (PAS) or Intersol. In an alternative embodiment, the photoactive agent may be combined with the additive solution in container 74. In any event, the additive solution and photoactive agent may be connected to integrated fluid circuit 54 through a pre-attached spike port 76 that includes a filter to ensure sterile connection and delivery of the agent and additive to the platelets. As shown in FIG. 6, connection of the additive and agent may occur at cassette 56c (or elsewhere in circuit 50).

Figure 4:
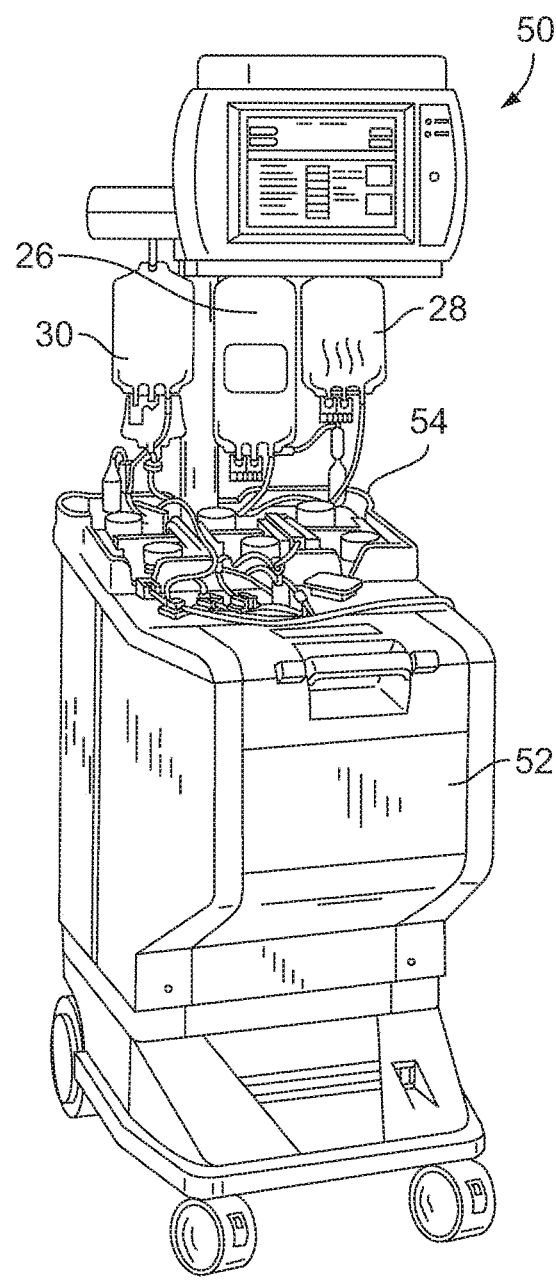
FIG. 4 shows the reusable hardware unit with the integrated fluid circuit mounted thereon.

While a discussion of platelet collection is beyond the scope of the present application, platelets for pathogen inactivation may be collected by known automated apheresis devices, such as the Amicus® Separator, available from Fenwal, Inc., of Lake Zurich, Ill. FIGS. 4 and 5 show a representative separation device useful in the separation and collection of platelets and the delivery of the additive solution described herein. The separator 50 includes a hardware component 52 and a disposable fluid circuit (e.g., integrated fluid circuit in accordance with the present disclosure) 54 mounted thereon. In one embodiment, the separation principle used by the separator is based on centrifugation, but an automated separator based on a different separation principle may also be used.

With respect to the device shown in FIGS. 4 and 5, a rotating centrifuge is housed within hardware component 52. Fluid circuit 54 includes the plastic containers for holding fluid, and tubing defining flow paths for movement of the blood, blood components and other fluids through the fluid circuit of kit 54. Disposable and integrated fluid circuit 54 includes one or more cassettes 56 (i.e., cassettes 56a, 56b and 56c shown in FIG. 4) which interface with the front panel of hardware component 52. Cassettes 56a, 56b and 56c include flow paths and valve stations. A series of pneumatically or electrically operated valves under the control of a pre-programmed controller of hardware component 52 selectively allow and restrict flow through the flow paths of the cassette and ultimately through the tubing of circuit 54. Integrated fluid circuit 54 further includes a processing chamber shown generally at 57 of FIG. 5 (which is mounted on a rotor/spool of the centrifuge). Processing chamber 57 has a sub-chamber 58 wherein blood or blood components are separated under the influence of centrifugal force (i.e., the "separation chamber") and a sub-chamber 59 where blood components from sub-chamber 58 can be further processed, separated and/or collected (i.e., the "concentration chamber"). Details of an automated separator suitable for use with the systems and methods described herein are set forth in U.S. Pat. Nos. 9,402,866; 5,427,509; 6,312,607; 6,582,349 and U.S. Patent Application Publication 2009/0211987, the entire contents of all of which are incorporated herein by reference.

Blood drawn from a volunteer donor may be centrifugally processed in separation sub-chamber 58 of processing chamber 57 to separate platelets from other blood components to obtain a platelet rich plasma suspension (i.e. platelets suspended in plasma). The platelet rich plasma may be conveyed from sub-chamber 58 to sub-chamber 59 where additional plasma may be removed to obtain platelet concentrate. The platelets are collected in illumination/collection container 60 which, as described above is part of the integrated fluid circuit 54. Providing a unitary illumination and collection container 60 also avoids the need to connect a collected platelet product to a separate pathogen inactivation kit as shown in FIG. 3.

The invention claimed is:

1. A fluid processing system comprising:
   a. a reusable hardware unit comprising a rotatable separator;
   b. an integrated fluid circuit configured for mounting onto said reusable hardware unit, said circuit comprising one or more fluid processing cassettes, a blood access device, a separation chamber, a blood component illumination/collection container and a compound adsorption device, wherein said blood component illumination/collection container is made of a material selected to transmit light of a selected wavelength.

2. The fluid processing system of claim 1 wherein said compound adsorption device is in openable flow communication with and downstream of said blood component illumination/collection container.

3. The fluid processing system of claim 1 wherein said integrated fluid circuit comprises one or more containers in openable flow communication with a container housing compound adsorption device.

4. The fluid processing system of claim 1 wherein said integrated fluid circuit comprises a fluid processing cassette configured to establish flow communication with a container of a blood component additive solution.

5. The fluid processing system of claim 4 wherein said container is associated with a source of a photoactive agent.

6. The fluid processing system of claim 5 wherein said container includes a combination of said blood component additive solution and said photoactive agent.

7. The fluid processing system of claim 5 wherein said photoactive agent is in a container associated with said container of said blood component additive solution.

8. The fluid processing system of claim 4 comprising a sterile connection between said container of said additive solution and said integrated fluid circuit.

9. The fluid processing system of claim 8 wherein said container of said additive solution further comprises a pre-attached spike port.

10. The fluid processing system of claim 1 wherein said rotatable separator comprises a centrifuge.

* * * * *